(12) United States Patent
McKinney et al.

(10) Patent No.: US 12,239,464 B2
(45) Date of Patent: *Mar. 4, 2025

(54) CATHETER FOR MONITORING PRESSURE

(71) Applicant: Sentinel Medical Technologies, LLC, Boca Raton, FL (US)

(72) Inventors: Timothy McKinney, Boca Raton, FL (US); Marc-Alan Levine, Pottstown, PA (US)

(73) Assignee: Sentinel Medical Technologies, LLC, Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/120,455

(22) Filed: Mar. 13, 2023

(65) Prior Publication Data
US 2023/0210466 A1    Jul. 6, 2023

Related U.S. Application Data

(62) Division of application No. 17/127,509, filed on Dec. 18, 2020, now Pat. No. 11,617,543.
(Continued)

(51) Int. Cl.
*A61B 5/00* (2006.01)
*A61B 5/01* (2006.01)
(Continued)

(52) U.S. Cl.
CPC .............. *A61B 5/6853* (2013.01); *A61B 5/01* (2013.01); *A61B 5/036* (2013.01);
(Continued)

(58) Field of Classification Search
CPC ......... A61B 5/6853; A61B 5/01; A61B 5/036; A61B 5/14551; A61B 5/205;
(Continued)

(56) References Cited

U.S. PATENT DOCUMENTS 3,721,229 A    3/1973 Panzer
4,192,319 A    3/1980 Hargens et al.
(Continued)

FOREIGN PATENT DOCUMENTS

CA    2961757    3/2016
CN    201267504    7/2009
(Continued)

OTHER PUBLICATIONS

3303EP Search Report 18725349, Dated Dec. 10, 2023.
(Continued)

*Primary Examiner* — May A Abouelela
(74) *Attorney, Agent, or Firm* — Neil D. Gershon

(57) ABSTRACT

A catheter insertable into a cavity of a patient for monitoring pressure including a first lumen for drainage from the cavity and an expandable balloon. The balloon has a liquid containing chamber to monitor pressure within the cavity of the patient as pressure on the outer wall of the balloon deforms the balloon and compresses the liquid within the balloon. An exit port provides passage of air from an interior of the balloon to outside the catheter. A membrane has plurality of pores dimensioned to enable passage of air but prevent passage of the liquid therethrough. A pressure sensor communicates with the liquid containing chamber for measuring pressure based on compression of liquid caused by deformation of the expanded balloon.

17 Claims, 8 Drawing Sheets

Related U.S. Application Data

(60) Provisional application No. 62/954,799, filed on Dec. 30, 2019.

(51) Int. Cl.
*A61B 5/03* (2006.01)
*A61B 5/1455* (2006.01)
*A61B 5/20* (2006.01)
*A61M 25/10* (2013.01)
*A61M 27/00* (2006.01)
*A61M 39/10* (2006.01)

(52) U.S. Cl.
CPC .......... *A61B 5/14551* (2013.01); *A61B 5/205* (2013.01); *A61B 5/4356* (2013.01); *A61B 5/6874* (2013.01); *A61M 25/1011* (2013.01); *A61M 25/10184* (2013.11); *A61M 25/10186* (2013.11); *A61M 27/00* (2013.01); *A61M 39/105* (2013.01); *A61B 2562/0247* (2013.01); *A61B 2562/0271* (2013.01); *A61M 2025/1077* (2013.01); *A61M 2205/3344* (2013.01); *A61M 2230/50* (2013.01)

(58) Field of Classification Search
CPC ................ A61B 5/4356; A61B 5/6874; A61B 2562/0247; A61B 2562/0271; A61M 25/1011; A61M 25/10184; A61M 25/10186; A61M 27/00; A61M 39/105; A61M 2025/1077; A61M 2205/3344; A61M 2230/50; A61M 25/1002; A61M 2025/0003
See application file for complete search history.

(56) References Cited

U.S. PATENT DOCUMENTS

| | | |
|---|---|---|
| 4,335,723 A | 6/1982 | Patel |
| 4,739,769 A | 4/1988 | Mathews et al. |
| 4,873,986 A | 10/1989 | Wallace |
| 4,901,731 A | 2/1990 | Millar |
| 4,976,692 A * | 12/1990 | Atad .................. A61M 25/1011 604/101.03 |
| 5,135,002 A | 8/1992 | Kirchner et al. |
| 5,167,237 A | 12/1992 | Rabin et al. |
| 5,398,692 A | 3/1995 | Hickey |
| 5,447,497 A | 5/1995 | Sogard et al. |
| 5,431,629 A | 7/1995 | Lampropoulos et al. |
| 5,433,216 A | 7/1995 | Sugrue et al. |
| 5,551,439 A | 9/1996 | Hickey |
| 5,566,680 A | 10/1996 | Urion |
| 5,570,671 A | 11/1996 | Hickey |
| 5,573,007 A | 11/1996 | Bobo, Sr. |
| 5,697,375 A | 12/1997 | Hickey |
| 5,707,358 A | 1/1998 | Wright |
| 5,951,497 A | 9/1999 | Wallace et al. |
| 5,980,485 A | 11/1999 | Grantz et al. |
| 5,984,879 A | 11/1999 | Wallace et al. |
| 6,021,781 A | 2/2000 | Thompson et al. |
| 6,115,624 A | 9/2000 | Lewis |
| 6,167,886 B1 | 1/2001 | Engel |
| 6,183,421 B1 | 2/2001 | Bobo |
| 6,231,524 B1 | 5/2001 | Wallace et al. |
| 6,248,083 B1 | 6/2001 | Smith |
| 6,434,418 B1 | 8/2002 | Neal et al. |
| 6,447,462 B1 | 8/2002 | Wallace et al. |
| 6,450,971 B1 | 9/2002 | Andrus et al. |
| 6,461,332 B1 | 10/2002 | Mosel et al. |
| 6,585,660 B2 | 7/2003 | Dorando |
| 6,648,879 B2 | 11/2003 | Joye et al. |
| 6,673,022 B1 | 1/2004 | Bobo et al. |
| 6,723,053 B2 | 4/2004 | Ackerman et al. |
| 6,827,710 B1 | 12/2004 | Mooney et al. |
| 6,890,307 B2 | 5/2005 | Kokate et al. |
| 7,081,096 B2 | 7/2006 | Brister et al. |
| 7,347,822 B2 | 3/2008 | Brockway et al. |
| 7,381,190 B2 | 6/2008 | Sugrue et al. |
| 7,654,967 B2 | 2/2010 | Bobo, Sr. |
| 7,722,544 B2 | 5/2010 | Williams et al. |
| 7,828,753 B2 | 11/2010 | Euliano, II et al. |
| 7,959,579 B2 | 6/2011 | Dijkman |
| 7,976,475 B2 | 7/2011 | Dijkman |
| 8,007,444 B2 | 8/2011 | Kokate et al. |
| 8,192,368 B2 | 6/2012 | Woodruff et al. |
| 8,235,426 B2 | 8/2012 | Pisula, Jr. et al. |
| 8,337,411 B2 | 12/2012 | Nishtala et al. |
| 8,360,988 B2 | 1/2013 | Bobo, Sr. et al. |
| 8,403,884 B2 | 3/2013 | Nishtala |
| 8,491,503 B2 | 7/2013 | Zaiken et al. |
| 8,535,237 B2 | 9/2013 | Nishtala |
| 8,596,688 B2 | 12/2013 | Pisula, Jr. et al. |
| 8,626,316 B2 | 1/2014 | Mohl |
| 8,636,724 B2 | 1/2014 | Wiita et al. |
| 8,636,728 B2 | 1/2014 | Watson |
| 8,646,325 B2 | 2/2014 | Hoem et al. |
| 8,708,927 B2 | 4/2014 | Dijkman |
| 8,876,729 B2 | 11/2014 | Bobo, Sr. et al. |
| 9,046,205 B2 | 6/2015 | Whitaker et al. |
| 9,055,949 B2 | 6/2015 | Belfort |
| 9,101,314 B2 | 8/2015 | Shi |
| 9,107,695 B2 | 8/2015 | Horton et al. |
| 9,108,000 B2 | 8/2015 | Kassab |
| 9,126,008 B2 | 9/2015 | Kim |
| 9,167,973 B2 | 10/2015 | Steiner et al. |
| 9,393,353 B2 | 7/2016 | Alam et al. |
| 9,439,600 B2 | 9/2016 | Mohl |
| 9,440,043 B2 | 9/2016 | Arora et al. |
| 9,510,766 B2 | 12/2016 | Weed et al. |
| 9,511,209 B2 | 12/2016 | Drasler et al. |
| 9,534,721 B2 | 1/2017 | Lombardi, III |
| 9,597,140 B2 | 3/2017 | Mihalik |
| 9,622,670 B2 | 4/2017 | Burnett et al. |
| 9,623,201 B2 | 4/2017 | Gregory et al. |
| 9,655,555 B2 | 5/2017 | Burnett et al. |
| 9,662,058 B2 | 5/2017 | Burnett et al. |
| 9,695,966 B2 | 7/2017 | Lombardi, III et al. |
| 9,713,494 B2 | 7/2017 | Nabutovsky et al. |
| 9,717,472 B2 | 8/2017 | Ahmed et al. |
| 9,724,232 B2 | 8/2017 | Kassab et al. |
| 9,734,706 B2 | 8/2017 | Moon et al. |
| 9,757,545 B2 | 9/2017 | Kassab |
| 9,782,115 B2 | 10/2017 | Shi |
| 9,782,145 B2 | 10/2017 | Hart et al. |
| 9,848,790 B2 | 12/2017 | Pintel |
| 9,877,660 B2 | 1/2018 | O'Connell et al. |
| 9,895,103 B2 | 2/2018 | Hyde et al. |
| 9,913,585 B2 | 3/2018 | McCaffrey et al. |
| 9,931,044 B2 | 4/2018 | Burnett et al. |
| 9,931,122 B2 | 4/2018 | Burnett et al. |
| 9,943,352 B2 | 4/2018 | Mihalik |
| 10,004,551 B2 | 6/2018 | Burnett |
| 10,194,813 B2 | 2/2019 | Bharucha et al. |
| 10,206,575 B2 | 2/2019 | Al-Mayah |
| 10,238,307 B2 | 3/2019 | Schlumpf et al. |
| 10,314,488 B2 | 6/2019 | Samuelsson et al. |
| 10,368,872 B2 | 8/2019 | Franklin et al. |
| 10,376,679 B2 | 8/2019 | Cox et al. |
| 10,391,275 B2 | 8/2019 | Burnett et al. |
| 10,433,741 B2 | 10/2019 | Stimpson |
| 10,478,113 B2 | 11/2019 | Damaser et al. |
| 10,485,483 B1 | 11/2019 | Brody |
| 10,517,538 B2 | 12/2019 | Burnett et al. |
| 10,531,834 B1 | 1/2020 | Smith et al. |
| 10,532,193 B2 | 1/2020 | Fischer, Jr. et al. |
| 10,537,274 B2 | 1/2020 | Damaser et al. |
| 10,537,308 B2 | 1/2020 | Zhadkevich |
| 10,542,924 B2 | 1/2020 | Imran et al. |
| 10,568,686 B2 | 2/2020 | Lee |
| 10,617,313 B2 | 4/2020 | Smith |
| 10,631,788 B2 | 4/2020 | Brody |
| 10,743,780 B2 | 8/2020 | Hoem et al. |
| 10,750,999 B2 | 8/2020 | Parks et al. |
| 10,758,135 B2 | 9/2020 | Burnett et al. |

(56) References Cited

U.S. PATENT DOCUMENTS

| | | |
|---|---|---|
| 10,772,998 B2 | 9/2020 | Luxon |
| 10,773,059 B1* | 9/2020 | Sardesai ............ A61M 25/0053 |
| 10,786,651 B2 | 9/2020 | Edminster et al. |
| 11,065,418 B1* | 7/2021 | Brody .................... A61M 39/22 |
| 11,077,301 B2* | 8/2021 | Creasey ................. A61B 5/204 |
| 11,648,380 B2* | 5/2023 | McCloskey ........... A61M 31/00 |
| | | 604/515 |
| 2002/0143294 A1 | 10/2002 | Duchon et al. |
| 2002/0183628 A1 | 12/2002 | Reich et al. |
| 2003/0060800 A1 | 3/2003 | Ryan |
| 2003/0114835 A1 | 6/2003 | Noda |
| 2003/0163052 A1 | 8/2003 | Mott |
| 2003/0181856 A1 | 9/2003 | Goldman |
| 2004/0077976 A1 | 4/2004 | Wilson |
| 2004/0127813 A1 | 7/2004 | Schwamm |
| 2004/0171942 A1 | 9/2004 | Ackerman et al. |
| 2005/0015047 A1 | 1/2005 | Shah |
| 2005/0055043 A1 | 3/2005 | Foltz |
| 2005/0065408 A1 | 3/2005 | Benderev |
| 2005/0187430 A1 | 8/2005 | Aundal et al. |
| 2005/0197585 A1 | 9/2005 | Brockway et al. |
| 2005/0215989 A1 | 9/2005 | Abboud |
| 2005/0240211 A1 | 10/2005 | Sporri |
| 2005/0283092 A1 | 12/2005 | Gedebov |
| 2006/0073728 A1 | 4/2006 | Zaiken |
| 2006/0085022 A1 | 4/2006 | Hayes |
| 2006/0085024 A1 | 4/2006 | Pepper |
| 2007/0083126 A1 | 4/2007 | Marko et al. |
| 2007/0197963 A1 | 8/2007 | Griffiths et al. |
| 2007/0282219 A1 | 12/2007 | Holte |
| 2008/0027358 A1 | 1/2008 | Gregersen et al. |
| 2008/0077043 A1 | 3/2008 | Malbrain et al. |
| 2008/0103408 A1 | 5/2008 | Denton et al. |
| 2008/0139967 A1 | 6/2008 | Euliano |
| 2008/0146990 A1 | 6/2008 | Jenson et al. |
| 2009/0221993 A1 | 9/2009 | Sohi et al. |
| 2009/0240199 A1 | 9/2009 | Rahimsobhani |
| 2009/0306539 A1 | 12/2009 | Woodruff |
| 2010/0056952 A1 | 3/2010 | Liu |
| 2010/0069900 A1 | 3/2010 | Shirley |
| 2010/0094204 A1 | 4/2010 | Nishtala |
| 2010/0094328 A1 | 4/2010 | O'dea et al. |
| 2010/0113939 A1 | 5/2010 | Mashimo et al. |
| 2010/0113968 A1 | 5/2010 | Bobo |
| 2010/0168836 A1 | 7/2010 | Kassab |
| 2010/0249663 A1 | 9/2010 | Nishtala |
| 2011/0087109 A1 | 4/2011 | Swann |
| 2012/0035595 A1 | 2/2012 | Goedje |
| 2012/0041334 A1 | 2/2012 | Goedje et al. |
| 2012/0053441 A1 | 3/2012 | Kassab |
| 2012/0179063 A1 | 7/2012 | Bharucha et al. |
| 2012/0316460 A1 | 12/2012 | Stout |
| 2012/0316461 A1 | 12/2012 | Liu |
| 2013/0030262 A1* | 1/2013 | Burnett .................... A61B 5/01 |
| | | 600/484 |
| 2013/0046217 A1 | 2/2013 | Mooney |
| 2013/0066166 A1 | 3/2013 | Burnett et al. |
| 2013/0079662 A1 | 3/2013 | Damaser et al. |
| 2013/0085519 A1 | 4/2013 | Kiminami |
| 2013/0211221 A1 | 8/2013 | Sunnarborg |
| 2013/0231584 A1* | 9/2013 | Burnett .................. A61B 5/036 |
| | | 600/561 |
| 2014/0012305 A1 | 1/2014 | Horton et al. |
| 2014/0094716 A1 | 4/2014 | Zaiken et al. |
| 2014/0107550 A1 | 4/2014 | Paulson |
| 2014/0107573 A1 | 4/2014 | Wiita et al. |
| 2014/0128766 A1 | 5/2014 | Beran |
| 2014/0155745 A1 | 6/2014 | Duncan |
| 2014/0163415 A1 | 6/2014 | Zaiken |
| 2014/0200482 A1 | 7/2014 | Shi |
| 2014/0364835 A1 | 12/2014 | Allen |
| 2015/0042406 A1 | 2/2015 | Kovac et al. |
| 2015/0065807 A1 | 3/2015 | Greenberg et al. |
| 2015/0133799 A1 | 5/2015 | O'Connell et al. |
| 2015/0327836 A1 | 11/2015 | Stone et al. |
| 2015/0342512 A1 | 12/2015 | Shi |
| 2015/0366485 A1 | 12/2015 | Kassab |
| 2015/0366498 A1 | 12/2015 | Choi et al. |
| 2016/0029912 A1 | 2/2016 | Stimpson |
| 2016/0066831 A1 | 3/2016 | Hyde et al. |
| 2016/0074581 A1 | 3/2016 | Gerrans |
| 2016/0106323 A1 | 4/2016 | Ou et al. |
| 2016/0183819 A1 | 6/2016 | Burnett et al. |
| 2016/0220136 A1 | 8/2016 | Schultz |
| 2016/0249969 A1 | 9/2016 | Santoinanni |
| 2016/0256076 A1 | 9/2016 | Kassab |
| 2016/0310148 A1 | 10/2016 | Allen |
| 2016/0331294 A1 | 11/2016 | Imran et al. |
| 2016/0331451 A1 | 11/2016 | Nabutovsky et al. |
| 2016/0354028 A1 | 12/2016 | Damaser et al. |
| 2016/0354140 A1* | 12/2016 | Sharma .................. A61B 90/39 |
| 2016/0374576 A1 | 12/2016 | Ziaie et al. |
| 2017/0055874 A1 | 3/2017 | Papirov et al. |
| 2017/0071566 A1 | 3/2017 | Hart et al. |
| 2017/0100561 A1 | 4/2017 | Burnett |
| 2017/0128012 A1 | 5/2017 | Parks et al. |
| 2017/0136209 A1 | 5/2017 | Burnett et al. |
| 2017/0156610 A1 | 6/2017 | Quackenbush et al. |
| 2017/0156611 A1 | 6/2017 | Burnett et al. |
| 2017/0160175 A1 | 6/2017 | Al-Mayah |
| 2017/0209048 A1 | 7/2017 | Wiita |
| 2017/0258345 A1 | 9/2017 | Smith |
| 2017/0259035 A1 | 9/2017 | Smith et al. |
| 2017/0332955 A1 | 11/2017 | Burnett et al. |
| 2018/0049658 A1 | 2/2018 | Smith |
| 2018/0177458 A1 | 6/2018 | Burnett et al. |
| 2018/0184929 A1 | 7/2018 | Burnett et al. |
| 2018/0311469 A1 | 11/2018 | Wiita |
| 2018/0326190 A1 | 11/2018 | Nash |
| 2018/0344183 A1 | 12/2018 | McKinney et al. |
| 2018/0344184 A1 | 12/2018 | McKinney et al. |
| 2018/0344234 A1 | 12/2018 | McKinney et al. |
| 2018/0344249 A1 | 12/2018 | McKinney |
| 2018/0344250 A1* | 12/2018 | McKinney et al. . A61B 5/6853 |
| 2019/0133460 A1 | 5/2019 | Wine |
| 2019/0133532 A1 | 5/2019 | Zaiken |
| 2019/0282109 A1 | 9/2019 | Schlumpf et al. |
| 2019/0321588 A1 | 10/2019 | Burnett et al. |
| 2019/0343445 A1* | 11/2019 | Burnett .................... A61B 5/207 |
| 2019/0350634 A1* | 11/2019 | Jung, Jr. ................ A61B 18/02 |
| 2020/0029906 A1 | 1/2020 | Smith et al. |
| 2020/0046237 A1 | 2/2020 | Stimpson |
| 2020/0069332 A1* | 3/2020 | Callery .................. A61M 29/02 |
| 2020/0085378 A1 | 3/2020 | Burnett et al. |
| 2020/0164184 A1 | 5/2020 | McKinney et al. |
| 2020/0197019 A1 | 6/2020 | Harper |
| 2020/0237242 A1 | 7/2020 | Kaluzny et al. |
| 2020/0253536 A1 | 8/2020 | McKinney |
| 2020/0305742 A1* | 10/2020 | Ghodsian ........... A61B 5/02055 |
| 2020/0324037 A1 | 10/2020 | Bloomberg et al. |
| 2020/0383703 A1* | 12/2020 | Atad ..................... A61M 29/02 |
| 2020/0384241 A1* | 12/2020 | Herrera .................. A61B 5/204 |
| 2021/0000422 A1 | 1/2021 | McKinney |
| 2021/0046277 A1* | 2/2021 | Samoocha .............. B08B 13/00 |
| 2021/0052873 A1* | 2/2021 | Geva ..................... A61M 37/0092 |
| 2021/0128413 A1* | 5/2021 | Elia ........................ G16H 40/63 |
| 2021/0177355 A1* | 6/2021 | Govari .................. A61B 5/6869 |
| 2021/0187240 A1* | 6/2021 | Waitkus ................... A61B 5/20 |
| 2021/0244912 A1* | 8/2021 | Paz ........................ A61M 25/01 |
| 2021/0290243 A1* | 9/2021 | Franklin .......... A61B 17/12109 |
| 2021/0369185 A1* | 12/2021 | Janssen ............. A61M 25/1002 |
| 2022/0039751 A1* | 2/2022 | Chey ..................... A61B 5/6853 |

FOREIGN PATENT DOCUMENTS

| | | |
|---|---|---|
| CN | 204582261 | 8/2015 |
| CN | 105073040 | 11/2015 |
| CN | 205649494 | 10/2016 |
| EP | 0097454 | 1/1984 |
| EP | 365629705/2020 | 5/2020 |
| WO | WO 94/02195 | 2/1994 |
| WO | WO 1995/012351 | 5/1995 |
| WO | WO 2005/013834 | 2/2005 |
| WO | WO 2006/060248 | 6/2006 |

(56) References Cited

FOREIGN PATENT DOCUMENTS

| WO | WO 2011/053500 | 5/2011 |
|---|---|---|
| WO | WO 2012/006624 | 1/2012 |
| WO | WO 2012/006625 | 1/2012 |
| WO | WO 2012/122267 | 9/2012 |
| WO | WO 2014/043650 | 3/2014 |
| WO | WO 2014/160300 | 10/2014 |
| WO | WO 2014/210453 | 12/2014 |
| WO | WO 2015/191125 | 12/2015 |
| WO | WO 2016/049654 | 3/2016 |
| WO | WO 2016/204631 | 12/2016 |
| WO | WO 2017/156451 | 9/2017 |
| WO | WO 2018/136306 | 7/2018 |
| WO | WO 2018/182913 | 10/2018 |

OTHER PUBLICATIONS

Extended European Search Report mailed Mar. 2, 2020 for European Application No. EP 19210264.8.
A randomized comparison of microtip and air-charged catheter for the measurement of maximum urethral closure pressure, Ginekol Pol. 2012, 83: 586-589.
Abdominal pressure in the critically ill: measurement and clinical relevance, Intensive Care Med, 1999, 25: 1453-1458.
(Abstract only) "Caring for critically injured children: An analysis of 56 pediatric damage control laparotomies". J Trauma Acute Care Surg. May 2017; 82: 901-909.
(Abstract only) "Estimation of Intra-abdominal Pressure by Bladder Pressure Measurement: Validity and Methodology", The Journal of Trauma Injury, Infection, and Critical Care, Feb. 2001, 50: 297-302.
(Abstract only) "Intra-Abdominal Pressure Monitoring in Neonates", Pediatric Critical Car Med. Feb. 2016; 17: 172-173.
(Abstract only) "Saline volume in transvesical intra-abdominal pressure measurement: Enough is enough", Intensive Care Med., Mar. 2006; 32: 455-459.
De Waele J., et al., "Saline volume in transvesical intra-abdominal pressure measurement: Enough is enough", Intensive Care Med., Mar. 2006; 32: 455-459.
Determination of Intra-abdominal Pressure Using a Transurethral Bladder Catheter: Clinical Validation of the Technique, Anesthesiology, Jan. 1989, 70( 1 ), 47-50.
European Search Report EP 20850354.0 Dated Jul. 15, 2022.
European Search Report EP 20850354, Dated Oct. 6, 2022.
International search report and written opinion for international application PCT/US2018/028687 mailed Sep. 28, 2018.
International search report and written opinion for international application PCT/US2018/028693 mailed Sep. 28, 2018.
International search report for international application PCT/US2018/032467 mailed Sep. 5, 2018.
International search report for international application PCT/US2018/034781 mailed Sep. 5, 2018.
Is clinical examination an accurate indicator or raised intra-abdominal pressure in critically injured patents? CJS, Jun. 2000, 43, No. 3: 207-211.
Mark A. Fusco, et al., "Estimation of Intra-abdominal Pressure by Bladder Pressure Measurement: Validity and Methodology", The Journal of Trauma Injury, Infection, and Critical Care, Feb. 2001, 50: 297-302.
Measurement on intra-abdominal pressure in large incisional hernia repair to prevent abdominal compartmental syndrome, G Chir, Jan.-Feb. 2016; 37: 31-36.
Miguel A. Villalobos, et al., "Caring for critically injured children: An analysis of 56 pediatric damage control laparotomies". J Trauma Acute Care Surg. May 2017, 82: 901-909.
Mudit Mathur, MD, "Intra-Abdominal Pressure Monitoring in Neonates", Pediatric Critical Car Med. Feb. 20, 16; 17: 172-173.
Pressure Measurement Techniques for Abdominal Hypertension: Conclusions from an Experimental Model, Crit Care Res Pract., May 2015: 278139.
Product information for Intra Compartment Pressure Wick's / Slit Catheter Set up (Stryker).
Product information for Intra- Compartmental Pressure Monitor System (Stryker).
Product information for Your Continuous Pressure Monitoring System (Mammendorfer Institut für Physik und Medizin GMbH).
Prospective Study of Intra-Abdominal Hypertension and Renal Function after Laparotomy, British Journal of Surgery, 1999, 82, 235-238.
Rudra, Pallab, et al. "Recent Advances In Management of Pre-Eclampsia" Sep. 2011, British Journal of Medical Practitioners, vol. 4, No. 3 (Year: 2011).
Sawchuck, Diane, et al. "Pre-eclampsia renamed and reframed: Intra-abdominal hypertension in pregnancy" Nov. 2014, Medical Hypothese, 83, 619-632 (Year: 2014).
Study of the occurrence of intra-abdominal hypertension and abdominal compartment syndrome in patients of blunt abdominal trauma and its correlation with the clinical outcome in the above patents, World J Emerg Surg. Feb. 11, 2016; 11: 9.
The Measurement of Intra-Abdominal Pressure as a Criterion of Abdominal Re-exploration, 1984 Ann Surg., 199: 28-30.
"The neglected role of abdominal compliance in organ-organ interactions", Critical Care. Mar. 2016; 1-10.
User's Manual for Compartmental Pressure Monitoring System. For continuous measurement of intra compartment pressure (Synthes).

* cited by examiner

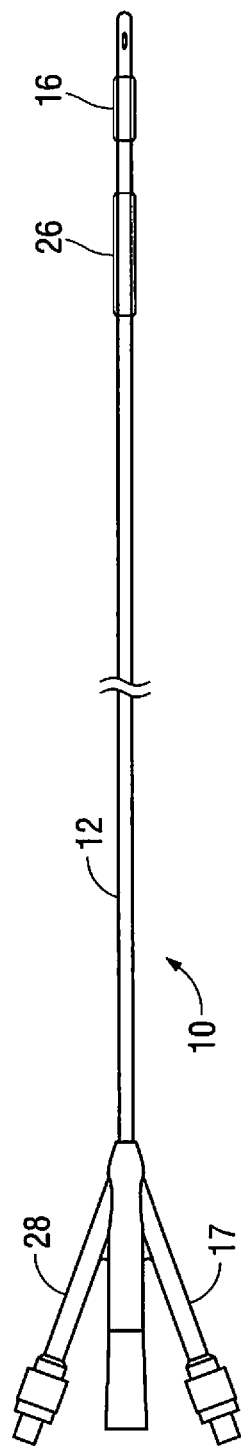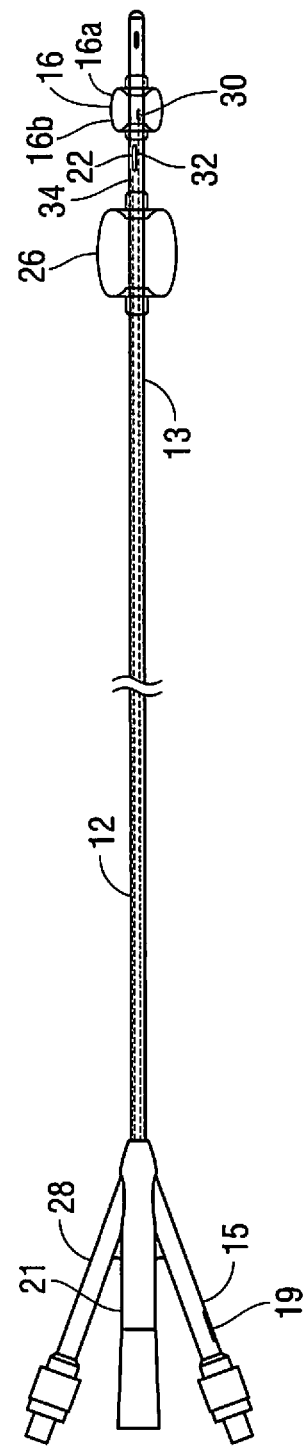

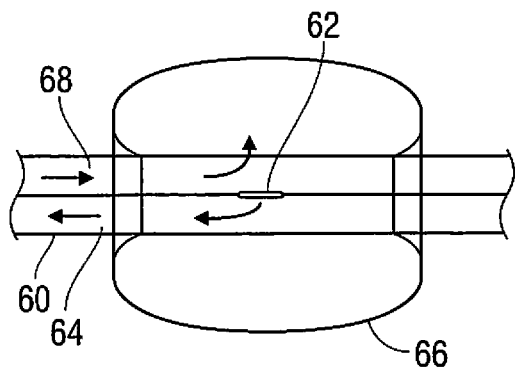 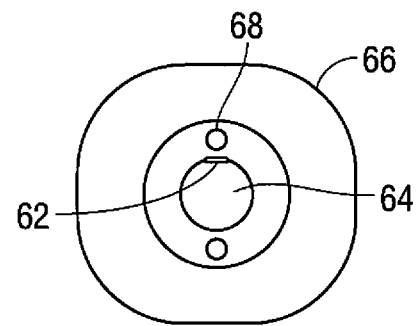
FIG. 5A  FIG. 5B
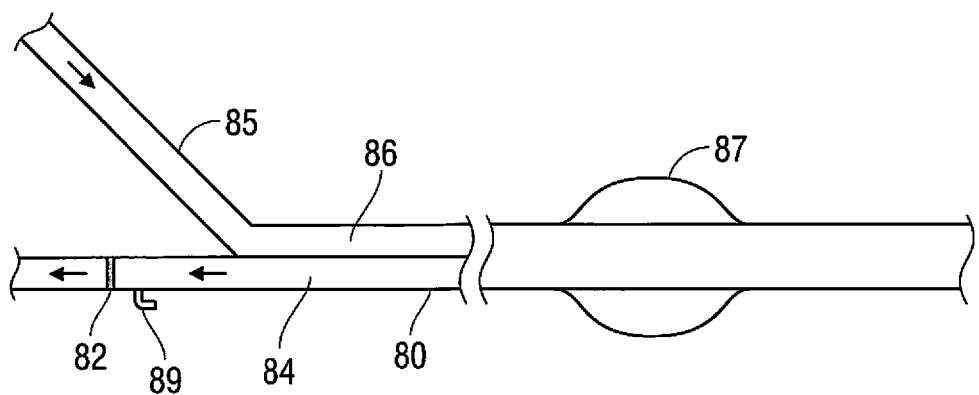
FIG. 6
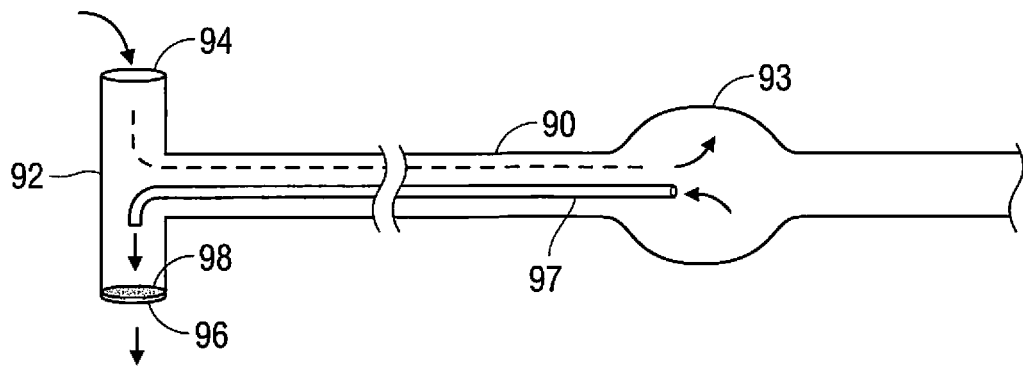
FIG. 7

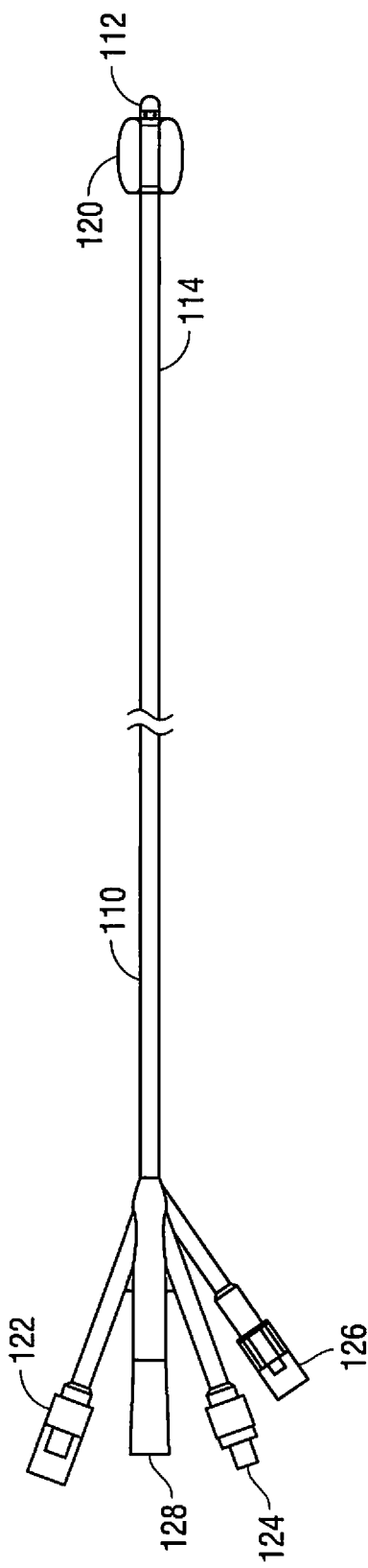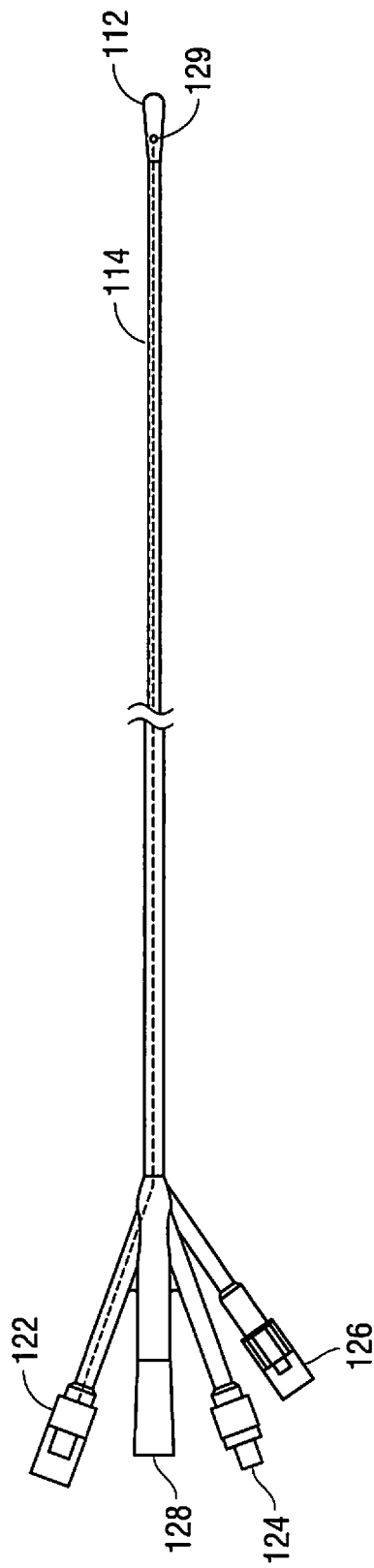
FIG. 8
FIG. 9

CATHETER FOR MONITORING PRESSURE

This application is a divisional of application Ser. No. 17/127,509, filed Dec. 18, 2020, which claims priority from provisional application 62/954,799, filed Dec. 30, 2019. The entire contents of each of these applications are incorporated herein by reference.

BACKGROUND OF THE INVENTION

1. Field of the Invention

This application relates to a device and method for monitoring pressure in a body cavity.

2. Background

Traditionally, physicians relied on visual cues or physical examination to detect increase in intra-abdominal pressure (IAP). More recently Dr. Kirkpatrick and colleagues, in an article "Is Clinical Examination an Accurate Indicator of Raised Intra-Abdominal Pressure in Critically Injured Patients," CJS, June 2000, 43, No. 3, 207-211, showed that IAP measured through the patient's bladder was significantly more accurate than physical examination. That is, it was demonstrated that the clinical abdominal examination was insensitive and inaccurate when compared with urinary bladder pressure measurements.

Various tools for measuring IAP have been developed over the years. Many researchers have documented IAP measurements through almost every natural or manmade orifice in the body. Earlier crude forms of measuring IAP used bladder catheters, nasogastric tubes, and rectal tubes attached to a manometer. The nasogastric or the rectal route was better suited in rare cases of bladder rupture or situations where bladder catheters were contraindicated. However, due to local interferences, the nasogastric and the rectal tube measurements were neither reproducible nor logical as were the bladder catheters.

Thus, measuring of IAP through the bladder became more suitable. In 1989 Iberti and colleagues in an article entitled, "Determination of Intra-abdominal Pressure Using a Transurethral Bladder Catheter: Clinical Validation of the Technique," Anesthesiology, January 1989, 70(1), 47-50, validated the correlation of IAP using a catheter inserted in the bladder. Their study was key in using bladder pressure as the gold standard for measuring IAP. In 1995, Kron and colleagues published a study in "The Measurement of Intra-Abdominal Pressure as a Criterion for Abdominal Re-exploration, 1984 Ann Surg., 199. 28-30, comparing catheters in various body locations for measuring IAP. They measured IAP from the stomach using a nasogastric tube, from the rectum using a modified rectal tube, from the bladder using a modified bladder catheter, and direct abdominal pressure using a laparoscopic insufflator needle. They found that the bladder catheter had the best measurement of IAP and that the gastric and the rectal catheter measurements were less reliable due to dependence on the position of the catheter. Thus, clinicians generally agreed that the urinary bladder is the best-suited location for measurement of IAP.

The need for measuring IAP has become more important as physicians increasingly realized that organ failure and death were directly related to increase in IAP in certain high-risk patients. High abdominal pressure has been found to cause a decrease in function of the intestines, liver and blood vessels resulting in adverse consequences for the patients. Consequently, accurate measurement of IAP can help decrease patient morbidity and mortality. It has also been more recently discovered that pediatric and neonate population may also have need for IAP measurement to determine specific conditions.

Currently, there are few products available on the market to measure the IAP through the bladder. One device, the Bard IAP device, has a "valve clamp" which diverts urine from the main catheter drainage channel to measure IAP via converting hydrostatic pressure to a readable pressure gauge. This mechanism of IAP measurements is archaic and does not provide continuous pressure measurement when used with the standard 2-channel bladder drainage catheter. Two other manufacturers, Holtech and ConvaTec, also use a column of urine by connecting their kit to an existing bladder catheter. Their systems are cumbersome and the IAP readings are also not continuous. Biometrix has developed an IAP monitoring device which like other manufacturers relies on tapping into the main bladder drainage catheter, using a valve to measure the hydrostatic pressure. In 2008 Sugrue and colleagues, in an article "Prospective Study of Intra-Abdominal Hypertension and Renal Function after Laparotomy, British Journal of Surgery, 1999, 82, 235-238, suggested the use of 3-channel bladder drainage catheter so that the smaller channel, which was used for bladder irrigation, could be used to attach a pressure-monitoring device. The use of an extra channel made it possible to have continuous bladder drainage while measuring the bladder pressure. However, this bladder catheter did not provide a continuous pressure read because intermittently the operator needed to add 50 ml of water or saline to the bladder to record the IAP pressure. Thus, the pressure reading at best was intermittent since pressure readings were not performed when fluid was being added to the bladder. Consequently, although this was a step toward increasing the amount of pressure readings/recordings, it still was unable to conduct continuous pressure monitoring. Furthermore, it was still the same cumbersome IAP device set up which required a skilled person to add water before each IAP reading. Control of the amount of water added is critical since adding too much water to the bladder can falsely increase the pressure readings and also increase infection risk, thus further complicating the use.

It has also been recognized that most patients that have a need for measurement of IAP also need to have continuous drainage of the urinary bladder and thus devices need to account for this process.

Consequently, current devices placed in the bladder for measuring pressure require a continuous water column to maintain pressure readings. Thus, they fail to measure IAP continuously but only measure pressure intermittently. They also all rely on tapping into an existing bladder drainage catheter, which adds complications. Furthermore, they do not reduce the complexity of the procedure since they require constant retrograde insertion of a relatively large amount of fluid into the bladder, e.g., 50 cc, which increases the ICU workload. Still further, these devices increase the risk of complications and infections associated with fluid injection into the bladder. Fluid injection is also complicated since it needs to be closely monitored since too much fluid in the bladder can give false elevation of IAP readings, causing clinicians to take unnecessary steps in response to what is mistakenly believed is excess IAP.

It would therefore be advantageous to provide a device insertable into the bladder that accurately measures abdominal pressure without requiring adding water to the bladder to obtain such pressure readings. Such device would advantageously avoid the complications and risks associated with such fluid insertion. Furthermore, it would be advantageous if such device could continuously measure bladder pressure without interruption. This would advantageously enable a constant monitoring of IAP so critical time periods are not missed. It would further be advantageous to provide a device that improves the accuracy of the pressure reading in the bladder to more accurately determine IAP so necessary steps can be taken to address IAP only when warranted. Still further, it would be advantageous if such device could satisfy the foregoing needs and provide these enumerated advantages while being simple to use so that so that any of the clinical staff with basic knowledge of bladder catheter insertion will be able to insert the device without relying on specially trained staff members. It would also be advantageous to provide such devices with these advantages for insertion into other body cavities for accurately measuring pressure within the cavity.

SUMMARY

The present invention overcomes the deficiencies and disadvantages of the prior art. The present invention provides catheters insertable into various regions of the patient such as the bladder to measure intra-abdominal pressure or maternal uterine contraction pressure, the uterine cavity to measure intrauterine pressure, the abdominal cavity, etc. The catheters can be used for example in rectal, abdominal, esophageal, cardiac, etc, procedures. The catheters of the present invention utilize a fluid column to measure pressure across a large surface area, and thus, accurately determine pressure, and enable pressure to be measured continuously.

The present invention in some embodiments provides a catheter insertable into the cavity of the patient to determine pressure without requiring insertion of water or other fluid into the body cavity. This avoids risks associated with retrograde filling of the bladder with water as such retrograde filling not only increases the complications and workload for the intensive care (IC) staff and can create inaccuracies by providing false elevation of IAP readings, but can adversely affect the patient by increasing the risk of infection. Furthermore, by avoiding refilling of the bladder, bladder pressure can be measured continuously. This is because in devices requiring filling the bladder with water, water needs to be periodically added to the bladder to replace the water drained from the bladder and measurement readings are interrupted during water insertion. Due to these repeated interruptions, pressure cannot be read continuously. Note in some cases, as much as 50 cc of fluid needs to be repeatedly added to the bladder. In some embodiments, the balloon acts as a transmission medium.

In accordance with one aspect of the present invention, a catheter is provided which is insertable into a patient for monitoring pressure, the catheter comprising a first lumen having a wall and at least one side opening in the wall for drainage from the cavity, a second lumen, and an expandable balloon at a distal portion of the catheter. The second lumen communicates with the balloon. The balloon has an outer wall and receives liquid to move from a first condition to a more expanded condition, the balloon expanding radially outwardly with respect to the catheter. The balloon has a liquid containing chamber to monitor pressure within the cavity of the patient as pressure on the outer wall of the balloon deforms the balloon and compresses the liquid within the balloon. An exit port provides for passage of air from an interior of the balloon to outside the catheter as liquid is inserted into the balloon. A membrane is provided having a plurality of pores dimensioned to enable passage of air but prevent passage of the liquid therethrough. A pressure sensor communicates with the liquid containing chamber for measuring pressure based on compression of liquid caused by deformation of the expanded balloon.

In some embodiments, the catheter includes an additional lumen and a stabilizing balloon. The additional lumen communicates with the stabilizing balloon to inflate the stabilizing balloon to stabilize the position of the catheter, the stabilizing balloon positioned proximal of the expandable balloon.

In some embodiments, the catheter includes a side port at a proximal end and the membrane is positioned within the side port. In some embodiments, the membrane is positioned at a distal portion of the catheter within the balloon. In other embodiments, the membrane is positioned at a proximal portion of the catheter and is in the second lumen. In some embodiments, the catheter includes a T-connector and the membrane is positioned within a first portion of the T-connector. In some embodiments, the catheter includes a valve to open and close flow of air through the membrane of the catheter.

In some embodiments, the catheter includes a second expandable balloon, the expandable balloon and second balloon extending radially on opposing sides of the catheter. The side opening can in some embodiments be positioned between the first and second expandable balloons.

In some embodiments, the catheter has a third lumen and a temperature sensor is positioned within the third lumen to measure core body temperature.

In accordance with another aspect of the present invention, a catheter insertable into a cavity of a patient for monitoring pressure is provided. The catheter includes a first lumen having a wall and at least one side opening in the wall for drainage from the cavity, a second lumen, and an expandable first balloon at a distal portion of the catheter, the second lumen communicating with the first balloon. The first balloon has a distal portion and a first outer wall, the first balloon receiving fluid to move from a first condition to a more expanded condition. In the first condition, the balloon has a distal portion protruding distally of the catheter to cover a tip of the catheter and a proximal portion within the catheter, and upon expansion of the balloon, the balloon exits a distal opening of the catheter and expands radially distally of the catheter distal opening. The balloon has a fluid containing chamber to monitor pressure within the cavity of the patient as pressure on the outer wall of the first balloon deforms the balloon and compresses the fluid within the first balloon. A pressure sensor communicates with the fluid containing chamber for measuring pressure based on compression of fluid caused by deformation of the first balloon resulting from deformation of the first balloon.

In some embodiments, the catheter includes an exit port for passage of air from an interior of the first balloon to outside the catheter, the exit port including a membrane having a plurality of pores dimensioned to enable passage of air but prevent passage of the liquid.

In some embodiments, the catheter includes an additional lumen and a stabilizing balloon. The additional lumen communicates with the stabilizing balloon to inflate the stabilizing balloon to stabilize the position of the catheter, the stabilizing balloon positioned proximal of the expandable balloon.

In some embodiments, the catheter includes a temperature sensor.

In some embodiments, the side opening for drainage is positioned proximal of the first balloon.

In some embodiments, the first balloon and stabilizing balloon are composed of different materials.

In accordance with another aspect of the present invention, a method for measuring pressure within a body cavity is provided comprising the steps of:
a) inserting into the body cavity a catheter having a first channel, a second channel, a permeable membrane and a first balloon, the first balloon having region to receive liquid;
b) inserting liquid into the first balloon to expand the first balloon and force air out of the first balloon, the air forced from the first balloon flowing through the first channel in the catheter to exit from the catheter, the membrane enabling passage of air therethrough and prohibiting passage of the liquid therethrough; and
c) obtaining multiple pressure readings within the body cavity during a procedure based on deformation of the first balloon.

In some embodiments, multiple pressure measurements are taken without requiring insertion of fluid into the body cavity.

In some embodiments, the method further comprises the step of measuring body temperature via a temperature sensor positioned within the catheter.

In some embodiments, the catheter includes a side port at a proximal end and the membrane is positioned within the side port. In some embodiments, the membrane is positioned at a distal portion of the catheter. In some embodiments, the method includes the step of opening a valve to open flow of air through the membrane of the catheter.

BRIEF DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein:

FIG. 1A is a side view of a first embodiment of the catheter of the present invention having a pressure balloon and a stabilizing balloon, both balloons shown in the deflated (collapsed) condition;

FIG. 1B is a side view similar to FIG. 1A showing the two balloons in the inflated (expanded) condition;

FIG. 5A is a side view of a portion of the catheter in accordance with an alternate embodiment of the present invention having a membrane adjacent the pressure balloon;

FIG. 5B is a transverse cross-sectional view of the catheter of FIG. 5A;

FIG. 6 is a side view of a portion of the catheter in accordance with an alternate embodiment of the present invention having a membrane adjacent the proximal end;

FIG. 7 is a side view of a portion of the catheter in accordance with an alternate embodiment of the present invention having a membrane in the proximal T-connector;

FIG. 8 is a side view of an alternate embodiment of the catheter of the present invention, the balloon shown in the deflated delivery condition;

FIG. 9 is a side view similar to FIG. 8 with a portion of the catheter wall removed for clarity;

DETAILED DESCRIPTION OF PREFERRED EMBODIMENTS

Increased abdominal pressure can cause many adverse conditions including diminishing the function of the intestines, liver, and blood vessels. Simply viewing or feeling the abdomen does not provide sufficient information or reading of health conditions.

It is recognized that urinary bladder pressure directly correlates to the intra-abdominal pressure. Although pressure readings can be determined by access to the esophagus or rectum, the bladder has been found to be the most accurate and the least invasive. In trauma or burn patients for example, time is critical and the less complicated the method for determining bladder pressure the better the clinical results.

It should be noted that the catheters of the present invention can be utilized for measuring other pressure in a patient and are not limited to intra-abdominal pressure. For example, they can be used to measure maternal uterine contraction measure by measuring bladder pressure. The catheters of the present invention can also be inserted into a variety of body cavities of the patient and can be used for monitoring pressure of various body regions.

These catheters can be used in various body cavities for measuring pressure and can be used without insertion of water or other fluid into the body cavity and thus have the numerous advantages associated with not requiring water as described herein.

Figure 1C:
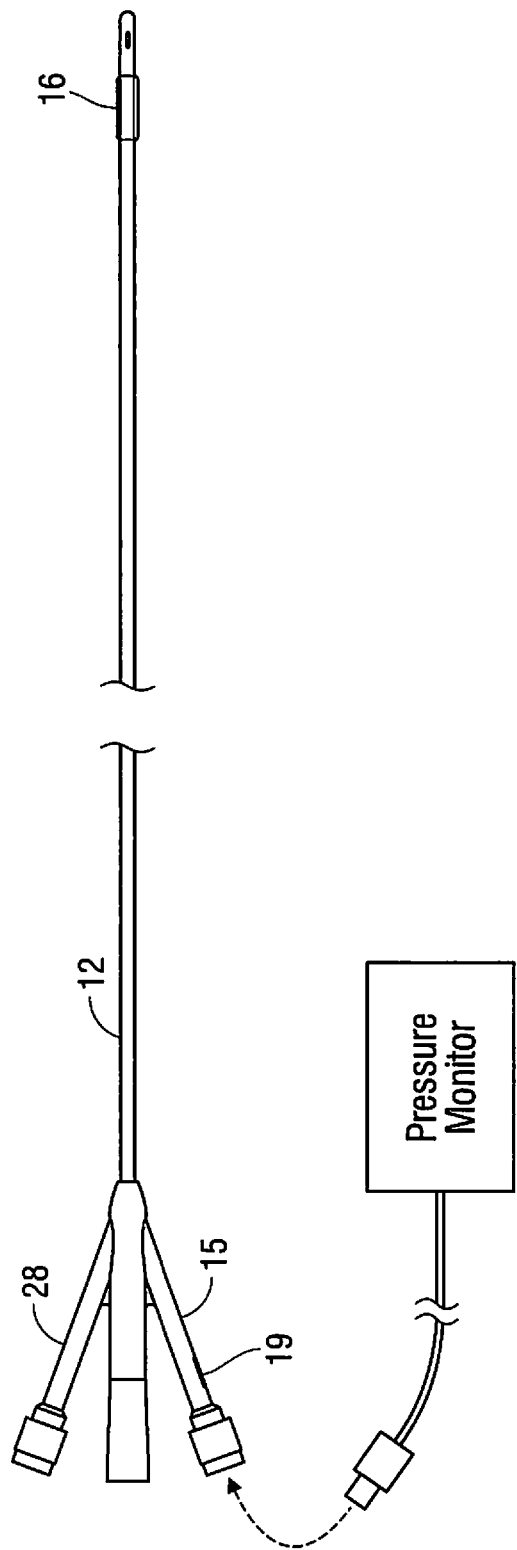
FIG. 1C is an enlarged side view of the catheter of FIG. 1A showing connection to a pressure monitor.

Referring now to the drawings and particular embodiments of the present invention wherein like reference numerals identify similar structural features of the devices disclosed herein, there is illustrated in FIGS. 1A-1B a catheter of a first embodiment of the present invention. The catheter (device) is designated generally by reference numeral 10 and is configured for insertion into and positioning within the bladder of the patient for measuring intra-abdominal pressure, although it can be used to measure pressure of other body regions and inserted into other body regions. This measurement is to check if the intra-abdominal pressure exceeds a specified threshold since if such threshold is exceeded, there is a risk to the patient as discussed above and steps need to be taken to reduce the pressure such as draining additional fluid from the abdomen, opening the abdomen, etc.

As used herein, the term fluid encompasses a liquid or a gas.

The catheter 10 of the present invention can in some embodiments include an alarm or indicator to alert the user if pressure within the bladder, which correlates to pressure within the abdomen, rises to an unacceptable level, i.e., beyond a threshold or predetermined value (pressure). The indicator or alarm can be on the catheter or alternatively on an external device such as the monitor. The alarm can also be connected via wireless connection to a phone or remote device to alert the appropriate personnel. The indicator or alarm can alternatively or in addition be activated if a change in pressure measurement exceeds a specified rate over a specified period of time. This would alert the staff to an imminent risk prior to intra-abdominal pressure exceeding a certain value, e.g., 20 mm Hg, since due to this link, the relationship between intra-abdominal pressure and abdominal cavity volume is believed to be linear up to an intra-abdominal pressure of 12-15 mm Hg and increasing exponentially thereafter. The alarm system can include a comparator for comparing the measured pressure (and/or temperature) to a threshold (predetermined) value, and if such threshold is exceeded, an indicator, e.g., an alarm, is triggered to indicate to the hospital personnel the excessive pressure and/or temperature.

Turning now to details of the catheter 10, which is also referred to herein as the device 10, the catheter 10 of this embodiment has an elongated flexible shaft 12 having a lumen (channel) 13 extending within the shaft 12 and communicating at its distal region with balloon 16 to fluidly communicate with balloon 16 to inflate the balloon. Expandable balloon 16 is utilized for monitoring pressure and is also referred to herein as the "pressure balloon." A fluid port 15 is positioned at a proximal region 17 of the catheter 10 for communication with an infusion source for infusion of fluid such as saline through the lumen 13 of shaft 12 and into the balloon 16. The catheter 10 is shown in FIG. 1A with balloon 16 in the deflated condition (position) and in FIG. 1B with the balloon 16 in the inflated condition (position). The shaft 12 can also include a second lumen (channel) and third lumen (channel) extending therein. In a preferred embodiment, the second lumen is the largest lumen and is configured for continuous drainage of bodily contents from the bladder and can be connected to a drainage bag for collection of urine. This lumen extends into lumen 21 at the catheter hub for drainage. The second lumen has a side opening 22 at a distal portion communicating with the bladder. The side opening 22 can be distal of the pressure balloon 16 or alternatively proximal of the balloon 16 such as between the pressure balloon 16 and the stabilizing balloon 26 as in the embodiment of FIG. 1B.

The third lumen terminates at its distal end within balloon 26 to fluidly communicate with balloon 26 to inflate the balloon 26. The balloon 26 is inflatable to stabilize the catheter 10 to limit movement of the catheter 10 to keep it in place within the bladder and is also referred to herein as "the stabilizing balloon" or "retention balloon." A fluid port 28 is positioned at a proximal region of the catheter 10 for communication with an infusion source for infusion of fluid through the third lumen and into the balloon 26. The balloon 26 can be filled with fluid, e.g., liquid such as water or saline, or a gas, e.g., air. In FIG. 1A, the balloon 26 is shown in the deflated condition and in FIG. 1B in the inflated condition.

The cross-sectional shapes of the lumens of catheter 10 and the other catheters disclosed herein can vary and can for example be circular, oval or other symmetrical or asymmetrical shapes in transverse cross section. As noted above, preferably the drainage lumen is the largest lumen but in alternate embodiments one or more of the other lumens could be larger than the drainage lumen.

The lumen 13 and space 16a within balloon 16 together form a closed fluid, chamber, i.e., the lumen 13 forming a fluid column. With the balloon 16 filled with saline or other liquid, pressure on the external wall of the balloon 16 will force the balloon 16 to deform inwardly, thereby compressing the liquid contained within the balloon space 16a and within the lumen 13.

A pressure sensor 30 can be located in a distal portion of the lumen 14 at the region of the balloon 16 and thus is positioned at the distal end of the fluid column. Thus, the pressure is sensed at the distal region as the sensor 30 detects change in fluid pressure in lumen 13 due to balloon deformation. Placement of the sensor 30 at a distal location provides a pressure reading closer to the source which in some embodiments/applications increases the accuracy because it reduces the risk of transmission issues by reducing the amount of interference which could occur due to water, air, clots, tissue, etc. if the transmission is down the lumen (fluid column).

Figure 2:
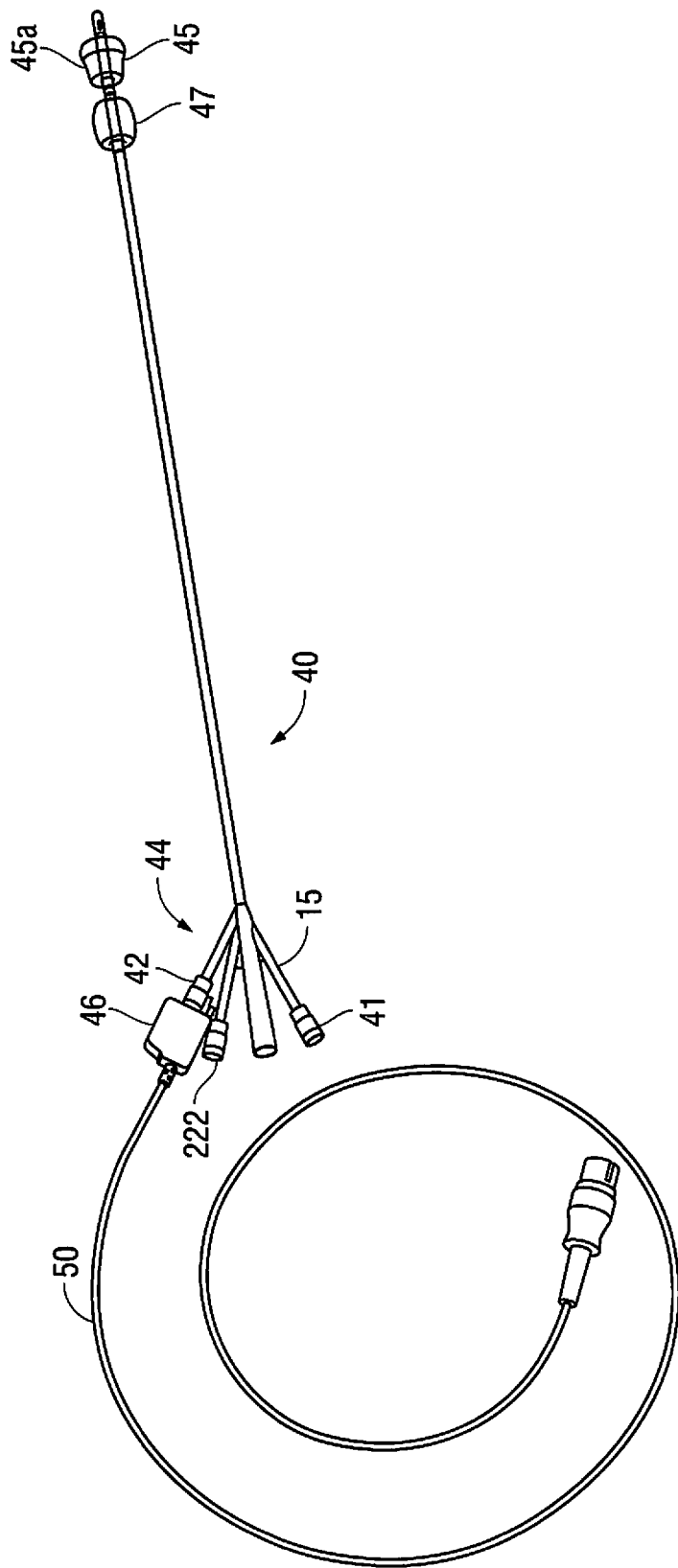
FIG. 2 is a perspective view of an alternate embodiment of the catheter showing a cable connected to the catheter for connection to a pressure monitor.

In alternate embodiments, the pressure sensor is at a proximal region of the catheter and can in some embodiments be connected at the hub of the catheter or in a side port of the catheter or in a proximal portion of the lumen. It can be or positioned outside the patient at a proximal region of the catheter or part of a connector attached to the catheter hub. FIG. 2 illustrates the sensor in the connector connected to the catheter.

The sensor 30 in the embodiment of FIGS. 1A and 1B is positioned within lumen 13 adjacent balloon 16, although alternatively it can be positioned within the balloon. The wire(s) 32 are shown extending through lumen 13, the sensor 30 and wire(s) 32 being of sufficiently small size so as not to interfere with liquid flow though lumen 13. The sensor 30 measures pressure of the bladder. The sensor 30 converts the variation in pressure to an electrical signal for transmission to an external monitor. The pressure sensor can also include a temperature sensor, or alternatively another sensor for sensing temperature could be provided, to measure core temperature of the body as seen inside the bladder. Transmission wire(s) 34 of the temperature sensor extend adjacent wire 32 through lumen 13 and terminate external of the catheter 10 for connection to an external monitor. The transducer can be wired directly to the monitor or alternatively wired to a converter external of the catheter for converting the signal received by the transducer and transmitting a signal to the monitor, e.g., a bedside monitor, to display the pressure readings. A cable with a monitor connector like cable 50 of FIG. 2A extends from the catheter 10 to a pressure monitor. The pressure readings can be displayed in quantitative form, graphical form or other displays to provide an indicator to the clinician of the bladder pressure. The monitor, or a separate monitor, can also display the temperature readings from sensor 30. Alternatively, the sensor/transducer can be connected to the monitor via a Bluetooth wireless connection.

Wires 32 and 34 can extend though lumen 13 and exit side port 15 for connection to a converter or monitor or alternatively can be inserted through the lumen 13, piercing the wall to enter the lumen distal of the side port.

The lumen 13 and space 16a within balloon 16 together form a closed fluid chamber, i.e., the lumen 13 forming a fluid column. With the balloon 16 filled (either fully filled or partially filled, although partially filled is preferred) with fluid such as saline, pressure on the external wall of the balloon will force the balloon to deform inwardly, thereby compressing the fluid contained within the balloon space 16a and within the lumen 13. The pressure sensor 30, located in a distal portion or alternatively a proximal portion of the catheter 10, detects change in fluid pressure in lumen 13 due to balloon deformation.

The pressure measurement occurs about a more circumferential area of the balloon 16 providing a pressure reading of a region greater than a point pressure sensor reading. Also, average pressure over an area of the bladder wall can be computed. Thus, the area reading gleans information on pressure over more of the bladder wall. Stated another way, the balloon has a relatively large surface area with multiple reference points to contribute to average pressure readings of the surface around it by the sensor.

The fluid is inserted through the side port 15 which communicates with lumen 13. The side port 15 at the catheter hub includes a membrane or filter 19 designed to enable the escape of air but prevent the escape of fluid. This enables removal of air to ensure filling of the pressure balloon 16. That is, when the fluid is inserted through the catheter lumen 13 into the balloon 16, air is forced out of the balloon 16 and proximally within the lumen of the catheter, through exit port and exiting the membrane 19. This provides a way to remove the air for accurate pressure readings without having to pull a vacuum. The membrane 19 can for example be a 0.2 micron filter with pores sized to enable outflow of air, but prevent outflow of saline or other liquid. In this manner, the saline remains in the catheter in a closed system and the air is forced out so the pressure can be accurately measured since the presence of air could create pressure reading inaccuracies. For example, air in the system could create an air lock and affect pressure reading. The membrane 19 is shown in the side port 15 of the catheter, however, it is also contemplated that it can be positioned in other regions of the catheter which is discussed in more detail below. The membrane can be composed of PTFE or other materials. A valve can be provided in some embodiments to provide two lines communicating with the balloon.

The air escape can be through an opening in the drainage lumen, covered with the membrane, which can communicate with the interior space of the pressure balloon, so air escapes through the drainage lumen. Alternatively, the air escape can be through another lumen of the catheter with an opening in the lumen communicating with the interior space of the balloon.

The balloon 16, as well as other balloons disclosed herein, can be composed of impermeable material, or in alternative embodiments, a permeable or semi-permeable material with an impermeable coating, depending on the material used and the fluid utilized for inflation, to prevent escape of air through the wall of the balloon 16. The fluid column is sealed at the distal end to prevent escape of air through the distal end.

The balloon 16 can be fully inflated and can press against the wall of the cavity in use. In some embodiments, depending on the material used and the fluid used for inflation, the balloon can be partially inflated to provide more compliancy to prevent the balloon from introducing artifact into the pressure reading which would diminish its accuracy.

Note in this embodiment, the stabilizing balloon 26 is positioned proximal of the pressure balloon 16. Also, in this embodiment, the stabilizing balloon 26 is larger than the pressure balloon 16. By way of example, the stabilizing balloon 26 can have a fully expanded diameter of about 23 mm and the pressure balloon 16 can have a fully expanded diameter of about 15 mm, although other dimensions or diameters for these balloons are also contemplated. By way of example, the stabilizing balloon 26 can have a capacity of about 10 cc (10 ml) of air, although other sizes/volumes are also contemplated. Note these sizes/volumes for both balloons are provided by way of example and other sizes are also contemplated. Alternatively, the stabilizing balloon can be the same size or smaller than the pressure balloon. Various shapes of the balloons are also contemplated.

Additionally, although the stabilizing balloon 26 is positioned proximal of the balloon 16, it is also contemplated that the balloon 26 be positioned distal of balloon 16. The axial spacing of the balloons 16, 26 enable the stabilizing balloon 26 to engage the bladder wall (or other cavity wall) to provide a sufficient radial force thereon for securing/mounting the catheter within the bladder without interfering with the function of balloon 16.

Note that although only one sensor is shown in, it is also contemplated that multiple sensors can be provided. Also, note that the sensor 30 is positioned in lumen 13 at a mid-portion of the balloon, i.e., just proximal where the opening in lumen 13 communicates with the interior 16a of the balloon 16. It is also contemplated that the sensor can be placed at another portion within the lumen 13, e.g., a more proximal portion, with respect to the lumen opening for the balloon. Also, the lumen opening for the balloon need not be at the mid portion of the balloon and can be at other regions of the balloon to communicate with the interior space 16a. Note if multiple sensors are provided, they can be positioned at various locations within the lumen 13.

As shown, the sensor 30 and its transmission wires are located in the same lumen 13 also used for initial inflation for balloon 16 and for the column. This minimizes the overall transverse cross-section (e.g., diameter) of the catheter 10 by minimizing the number of lumens since additional lumens require additional wall space of the catheter. However, it is also contemplated in an alternate embodiment the sensor is in a dedicated lumen separate from the inflation lumen 13. This can be useful if a larger sensor or additional wires are utilized which would restrict the inflation lumen if provided therein. This is also useful if a specific sized lumen for the sensor and wires is desired to be different than the sized lumen for the fluid column. In such embodiments, the catheter would have four lumens: 1) a lumen for drainage of the bladder which has a side opening at a distal end to communicate with the bladder; 2) a lumen for filling the pressure balloon; 3) a lumen for filling the stabilizing balloon; and 4) a lumen in which sensor 30 and its transmission wires 32 and temperature sensor wires 34 are contained. Note in some embodiments, separate lumens could be provided for the wires 32 and wires 34. Also, in some embodiments, a stabilizing balloon is not provided so the catheter can have one less lumen.

Turning now to the use of the catheter 10, the catheter 10 is inserted into the bladder. The stabilizing balloon 26 is inflated to secure the catheter 10 in place during the procedure by insertion of a fluid (liquid or gas) through side port 28 which is in fluid communication with the lumen communicating with balloon 26. The balloon 16 is inflated by insertion of saline or other liquid via a syringe through port 15 which is in fluid communication with lumen 13. Insertion/injection of saline forces the air out of the balloon 16 and proximally through the catheter 10 to exit through the membrane 19. The balloon 16 is sealed so that saline inserted through lumen 13 and into balloon 16 cannot escape through balloon 16. Thus, a closed chamber for the saline is formed comprising the internal space 16a of the balloon 16 and the internal lumen 13 communicating with the internal space 16a of balloon 16. With the balloon 16 inflated, pressure monitoring can commence. When external pressure is applied to an outer surface 16b of the balloon 16, caused by outward abdominal pressure which applies pressure to the bladder wall and thus against the wall of balloon 16, the liquid within the chamber is compressed. The sensor 30 at the distal end of lumen 13 (or in other regions of the catheter or attached to the catheter hub in alternate embodiments as described herein) provides continuous pressure readings, converted to an electrical signal by the transducer, and then electrically communicates through wire(s) 32 extending through lumen 13, exiting through the proximal side port 15 and connected to an external monitor. Note the wire can terminate at the proximal end in a plug in connector which can be connected directly to the monitor or alternatively plugged into a converter to convert the signals from the transducer in the embodiments wherein the converter is interposed between the wires and monitor to provide the aforedescribed graphic display. Although, the system is capable of continuous pressure and temperature monitoring, it can also be adapted if desired for periodic monitoring so the pressure and/or temperature readings can be taken at intervals or on demand by the clinician.

In the embodiments wherein an indicator is provided, if the measured pressure exceeds a threshold value, and/or a change in pressure measurement exceeds a specific rate over a specific time period, the indicator would alert the clinician, e.g., via a visual indication or an audible indication that the threshold is exceeded. The indicator in some embodiments can include an audible or visual alarm. In the embodiments having an indicator, the indicator can be provided on a proximal end of the catheter which extends out of the patient or the indicator can be part of an external component such as the monitor or a separate alarm system. A visual, audible, or other indicator can likewise be provided in any of the other embodiments disclosed herein to indicate if the measured temperature exceeds a predetermined value, and such indicator can include an alarm and can be part of the catheter or a separate component.

As discussed above, the pressure balloons disclosed herein have a large circumferential area (and large volume) to provide multiple reference points for pressure readings and to provide an average pressure to enable more accurate readings. In some embodiments, a pear shaped larger outer balloon is provided such as in the embodiment of FIG. 2A. The covers more surface area for pressure readings. The pear shape could in certain applications decrease the risk of obstructing the ureter and provide more tactile continuity of the balloon to the bladder wall giving a better transmission of abdominal pressure to the internal sensor. This pear shape in some applications is designed to conform to the shape of the bladder. The pressure balloon can be shaped such that a distal region has an outer transverse cross-sectional dimension, e.g., diameter, greater than an outer transverse cross-sectional dimension, e.g., diameter, of the proximal region such as in the embodiments of FIGS. 2 and 3. The pressure balloons of the embodiments herein can be symmetrically or asymmetrically shaped.

Figure 3:
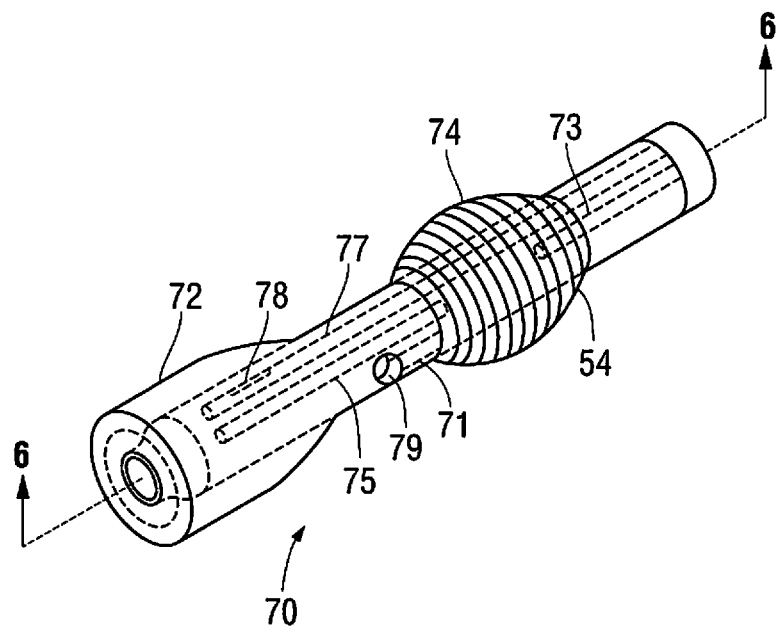
FIG. 3 is a perspective view of an alternate embodiment of a distal region the catheter of the present invention showing the balloon in the inflated condition.
Figure 4:
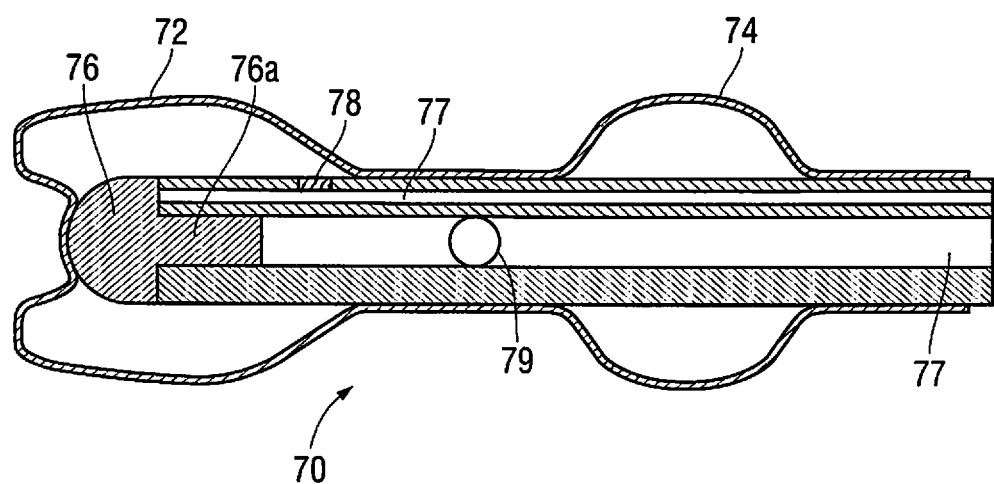
FIG. 4 is a cross-sectional view taken along line 6-6 of FIG. 3.
Figure 10:
FIG. 10 is a side view similar to FIG. 9 showing the balloon in the inflated condition.
Figure 11:
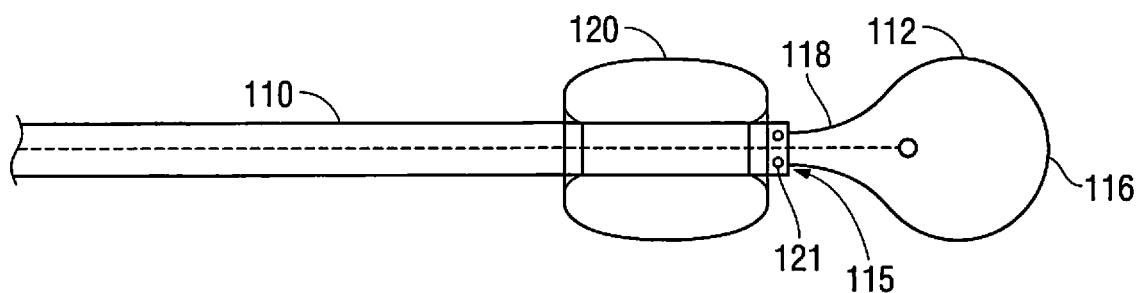
FIG. 11 is a side view of the distal portion of the catheter of FIG. 8 showing the balloon in the inflated condition.

FIGS. 3 and 4 illustrate an alternate embodiment of the pressure and stabilizing balloon. The stabilizing balloon 74 of catheter 70 is proximal of the pressure balloon 72 and has an oval like shape. The pressure balloon 72 is shown extending beyond the tip 76 of the catheter 70. Tip 76 has a proximal extension 76a positioned within the lumen 77. The catheter 70 has a filter or membrane 78 adjacent balloon 72 so that when balloon 72 is inflated with saline or other liquid, air is forced out of balloon 72 and travels through the catheter lumen 77 and through the membrane 78 to exit the catheter at a proximal end. A separate lumen 75 inflates pressure balloon 72. The pores of membrane 78 are dimensioned to allow escape of air but prevent escape of the inflation liquid. The membrane 78 is shown adjacent the pressure balloon 72 but can be positioned in other regions of the catheter 70, i.e. in the various locations disclosed herein, e.g., in a proximal portion of the catheter, in the catheter hub, etc. As in the embodiment of FIG. 1A, in the expanded position of the balloon 72, pressure on the wall of balloon 72 deforms the outer wall of the balloon 72 and compresses the liquid therein to provide pressure readings as disclosed herein. A drainage hole 79 can be provided between the stabilizing balloon 74 and pressure balloon 72 for drainage through lumen 71. A separate lumen is used to inflate the stabilizing balloon 74.

In the embodiment of FIG. 2, the pressure sensor/transducer are external to catheter 40 and mounted to port 42 at the proximal end 44 of catheter 40. More specifically, a transducer hub or housing 46 contains the sensor/transducer and is mounted to the angled side port 42. The hub 46 can be mounted over the port 42 and can be locked or secured thereto such as by a friction fit, snap fit, threaded attachment, a latch, etc. Thus, when external pressure is applied to an outer surface 45a of the balloon 45, caused by outward abdominal pressure which applies pressure to the bladder wall and thus against the wall of balloon 45, the fluid within the chamber (formed by the internal space of the balloon 45 and the lumen) is compressed. The sensor in the hub 46 attached to the catheter port provides continuous pressure readings, and then electrically communicates through cable 50 to an external monitor. Port 41 is for fluid insertion to inflate the stabilizing balloon 47.

The pressure balloons of the various embodiments can by way of example be made of urethane, although other materials are also contemplated such as silicone or EVA.

A temperature sensor, such as a thermocouple, is positioned within the catheter 40 at a distal end to measure core body temperature in the same manner as in FIG. 1A, with one or more wires extending from the sensor through the lumen. A connector, e.g., a male connector, is at the proximal terminal end of the wire and the transducer hub 46 includes a connector which receives the connector of the wire. When the hub 46 is mounted to port 42 of catheter 40, the connector of the wire is automatically connected to a connector carried by or within the hub 46 which is in communication with a temperature monitor, such as by cable 50. Other types of connectors/connections are also contemplated. Temperature readings can be taken at intervals or on demand by the clinician. The temperature monitor can be separate from the pressure display monitor or alternatively integrated into one monitor. Cable 50 can connect to the temperature monitor as well (directly or via a converter) or a separate cable extending from the hub 46 could be provided for connection to the temperature monitor.

FIGS. 5A and 5B, 6 and 7 illustrate alternate embodiments of the membrane for allowing the escape of air during filling of the balloon with saline or other fluid. Note these embodiments can have a stabilizing balloon in addition to the pressure balloon. In the embodiments of FIGS. 5A and 5B, catheter 60 has a filter/membrane 62 at a distal region of lumen 64 adjacent pressure balloon 66. Saline is inserted through lumen 68 which communicates with pressure balloon 66. As the balloon is being filled, the air is forced out of the balloon 66, passing through membrane 62 and traveling proximally in lumen 64 to exit in a vent in or adjacent a hub of the catheter at the proximal end. The membrane 62 has pores dimensioned to allow the escape of air but prevent the escape of saline so that during inflating the balloon, the saline cannot escape from the balloon 66 into lumen 64 through membrane 62.

In the embodiment of FIG. 6, catheter 80 has a membrane 82 positioned within a lumen 84 at the proximal end of the catheter. Liquid, e.g. saline, is inserted through port 85 to flow through lumen 86 to inflate the pressure balloon 87 which forces out air from the balloon 87 which flows through lumen 84 (which is in communication with balloon 87) to exit through membrane 82. The catheter 80 can include a valve 89 which can be turned on to allow passage of air through the membrane 82 and closed to prevent passage of air. The liquid is prevented from flowing out of the catheter when the valve is closed as well as when the valve is open since it cannot pass through the pores of the membrane 82. Note a valve can be provided in the catheters having the membrane placed in other regions of the catheter.

In the embodiment of FIG. 7, catheter 90 includes a T-connector 92 with an opening 94 for liquid, e.g., saline or water insertion, and opposing opening (vent port) 96 for escape of air. At opening 94, a luer or other connector enabling connection of a syringe or other device to fill the pressure balloon 93 is provided. The liquid inflates the pressure balloon 93 and forces the air out through exit opening 96. Membrane 98 is positioned within the T-fitting 92 to enable passage/escape of air and prevent passage of the other liquid, e.g. saline or water. In FIG. 7, one of the catheter lumens has a tube 97 positioned therein. This tube 97 has an opening communicating with the interior space of the pressure balloon 93 and extends back to the membrane 98. In alternate embodiments, the tube is not provided and air flows through the lumen for escape rather than through the tube. The balloon inflation lumen (channel) can be filled until water comes to the end to fill the channel which would force the air out of the system through the membrane 98. The membrane can alternatively be located in other portions of the catheter. The tube communicating with the membrane can be provided in the catheters of the other embodiments disclosed herein.

The membrane for passage of air can be provided at various regions of the catheter, e.g., adjacent the balloon, at the catheter hub, at a proximal region of the catheter, etc. Also, the membrane can be positioned within the drainage lumen or in a separate lumen which communicates with the interior space of the balloon. It can also be provided in a tube which extends through a lumen of the catheter and has an opening in communication with the interior space of the balloon. In some embodiments, the pressure sensor can be positioned in a chamber and the chamber can have air passage, e.g., a membrane, filter, and valve. The sensor can be connected to the catheter, and the air can be removed at the interface of the catheter and the sensor. A purge valve can be provided on the connector. The vent can be below (distally) but before the side ports of the catheter.

Figure 13:
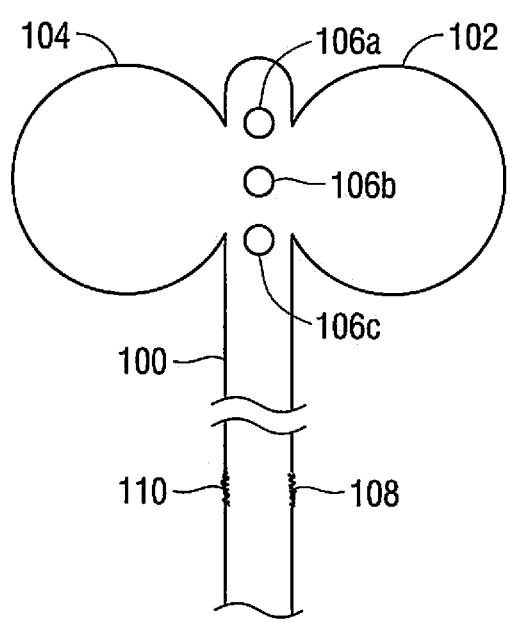
FIG. 13 is a top view of an alternate embodiment of the catheter of the present invention, the balloons shown in the inflated condition.

The membrane can also be utilized in a catheter with multiple pressure balloons as in the embodiment of FIG. 13. Catheter 100 has first and second pressure balloons 102, 104 extending radially on opposing sides of the catheter, i.e., positioned side by side. A plurality of drainage holes 106*a*, 106*b*. 106*c* are positioned in a side wall of the catheter 100 between the balloons 102, 104. A membrane is provided in catheter 100 either adjacent the balloon 102, 104 or at another region of the catheter 100 to enable escape of air from the balloon 102, 104 as they are inflated as described in the foregoing embodiments. In some embodiments, separate membranes 108, 110 can be provided for the lumens communicating with balloons 102, 104, respectively, for air escape. The balloons 102, 104 are filled with liquid such as saline or water and form a liquid chamber or column as described above. Pressure can be determined by pressure differentials between the two balloons or by reading both pressure balloons and taking an average of the two readings.

Figure 12:
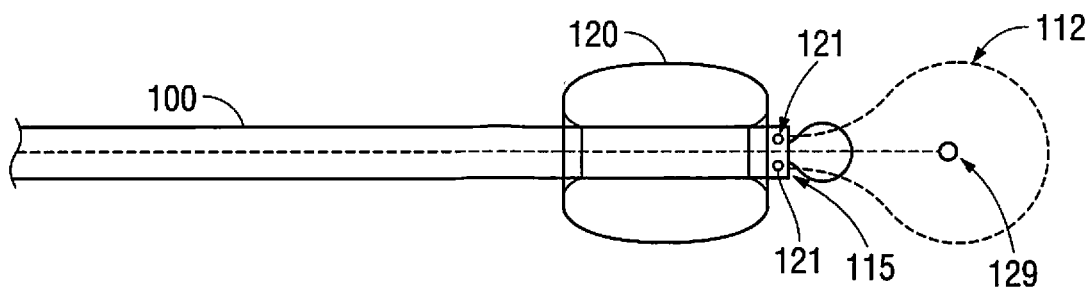
FIG. 12 is a side view of the catheter of FIG. 8 showing the balloon moving distally of the catheter in the inflated condition.

In the embodiment of FIGS. 8-12, the pressure balloon 112 extends distally of the catheter 110 in the non-expanded position to shield the tip of the catheter. As shown, catheter 110 has an outer pressure balloon 112 which during insertion is deflated and partially contained within the shaft 114. However, in this insertion position, a distal region 116 of balloon 112 extends forward of the distal end of the catheter 110. This shape creates a nose cone at the tip. The protruding pressure balloon 112 is preferably made of polyurethane, although other materials can be utilized. When the balloon is inflated, it slides/pops out of the distal end of the catheter shaft 114. Thus, as it opens up, it elongates out of the catheter body and the proximal portion is a smaller diameter so the distal opening 115 of catheter 110 becomes open for drainage. The catheter is shown in FIG. 12 with the balloon 112 illustrated in phantom lines in the expanded position. Additional drainage openings 121 can be provided in a side wall of the catheter 110. A stabilizing balloon 120 can be positioned proximal of the pressure balloon 112. The stabilizing balloon 120 can be made of silicon, although other materials are also contemplated. The catheter in some embodiments can be made of polyurethane, although other materials are also contemplated. The catheter hub has port 122 for fluid infusion to inflate/expand the pressure balloon 112, port 124 for drainage, and port 126 for fluid insertion to inflate/expand the stabilizing balloon 120. Temperature sensor (thermistor) 129 can be positioned adjacent or within the pressure balloon 112. Temperature sensor wires can extend through port 128.

Pressure balloon 112 can be filled with gas such as air to form a closed gas chamber for pressure monitoring. Alternatively, it can be filled with a liquid such as saline in which case the catheter (or connector) can include a membrane to allow escape of air as the pressure balloon is filled as in the embodiments described above.

As noted herein, the catheters of the present invention can be utilized for measuring other pressure in a patient and are not limited to intra-abdominal pressure nor limited to measuring bladder pressure.

In the catheters disclosed herein, thermistor can be placed adjacent the drainage opening for temperature readings, and the thermistor wire can extend through a lumen of the catheter, e.g., the drainage lumen, the pressure lumen or a separate lumen, for electrical connection to a temperature monitor.

The balloons of the catheters disclosed herein could include a coating such a parylene to change the modulus of the balloon. That is, such coating could stiffen the balloon so it is not to continuously expand under pressure, which could cause a reduced pressure reading. The coating can also cover all or part of the catheter which could add lubricity.

The balloons disclosed in the various embodiments can be coated to reduce their permeability. That is, to prevent escape of fluid, the balloons can be made of an impermeable material and/or the balloons can be made of a permeable material and coated with an impermeable material.

As noted herein, the catheters of the present invention can be utilized for measuring other pressure in a patient and are not limited to intra-abdominal pressure nor limited to measuring bladder pressure. Thus, the structure can be used for example with catheters to measure maternal uterine contraction pressure by measuring bladder pressure as in copending application Ser. No. 15/949,022, filed Apr. 9, 2018 (Publication No. 2018/0344250), the entire contents of which are incorporated herein by reference, and with catheters to measure the intrauterine pressure in the uterus and the fallopian tubes during HSG, SHG, HyCoSy, or SIS procedures or other procedures, as in co-pending application Ser. No. 15/978,072, filed May 11, 2018 (Publication No. 2018/0344183), the entire contents of which are incorporated herein by reference.

In embodiments disclosed herein, a digital pressure sensor can be used instead of an analog sensor.

The wire connector of the foregoing embodiments can plug into the openings of a connector positioned on or in the hub. The wire connector can be internal of the hub with an opening in the wall of the hub to enable access for the wire connector. Also note that alternatively the wire can include a female connector and the hub can have a male connector. Other types of connectors/connections are also contemplated.

In some embodiments the catheters disclosed herein can include a pulse oximetry sensor to measure oxygen saturation in the urethral or bladder tissue. The sensor can be located either proximal or distal to the pressure balloon and/or either proximal or distal to the stabilizing balloon. It could also alternatively be mounted within one of the balloons.

It is also contemplated that in some embodiments a backup system can be provided to determine pressure. The backup system can provide a double check of pressure readings to enhance accuracy. Such backup system can be used with any of the embodiments disclosed herein to provide a second pressure reading system. One example of such backup system is providing a pressure transducer/pressure sensor within the catheter lumen communicating with the pressure balloon, forming a "first system", plus a pressure transducer/pressure sensor at another region of the catheter or external of the catheter forming a "second system". The pressure sensors are electrically connected to a monitor which provides a graphic display of pressure readings. The catheter can also include a temperature sensor either as part of the pressure sensor adjacent the distal portion of the catheter or a separate component that can be positioned in the lumen.

In use of such backup system, the sensor provides continuous pressure readings, and such pressure readings can be confirmed by the proximal sensor. Such pressure readings can be performed continuously (along with continuous temperature monitoring) or alternatively can also be adapted if desired for periodic monitoring so the pressure and/or temperature readings can be taken at intervals or on demand by the clinician. Thus, pressure readings at a proximal end plus microtip pressure readings at the distal end are provided. The sensors can electrically communicate with an external monitor to display both pressure readings from the sensors, or alternatively, if the pressure readings are different, they can be averaged to display a single measurement. Other displays of information can be provided to display the information from the two sensors.

The sensors disclosed herein can be microtip sensors within the fluid lumen or balloon. In alternative embodiments, fiber optic sensors within the fluid lumen or balloon can by utilized to transmit circumferential/area pressure. The pressure transducers can be housed within the catheter or alternatively external to the catheter. Additionally, core temperature sensors can be part of the pressure sensor or a separate axially spaced component.

The multi-lumen catheters are easily inserted into the bladder in the same manner as standard bladder drainage catheters and enable continuous drainage of urine while continuously recording IAP without interrupting urine flow and without requiring retrograde filling of the bladder with water. The catheters also have a balloon providing a large reservoir (large capacity) and large circumferential area/interface for obtaining more information from the bladder over multiple reference points (rather than a single point sensor) that provides an average pressure to provide a more accurate assessment of the surrounding environment as pressure measurement is not limited to one side of the bladder but can determine measurements on the opposing side as well. The balloon can have a sufficiently large circumferential area so that it is in contact with the bladder wall, and in some embodiments, could distend the bladder wall, thus enabling pressure measurement without insertion of fluid into the bladder. When used in other body cavities for other pressure measurements, the pressure balloon of the multi-lumen or single lumen catheters disclosed herein can be of sufficiently large to contact or in some embodiments, distend the cavity wall, thus enabling pressure measurement without insertion of fluid into the cavity.

The catheters in some embodiments can be connected to a bedside monitor through either a wire or blue-tooth wireless connection. The system can also in some embodiments include an indicator or alarm system to alert the staff at the site as well as remote staff through wired or wireless connections to external apparatus, e.g., hand held phones or remote monitors.

As noted above, an alarm or indicator can be provided in some embodiments to alert the staff. The indicator can be a visual indicator such as a light, LED, color change, etc. Alternatively, or additionally, the indicator can be an audible indicator which emits some type of sound or alarm to alert the staff. The indicator can be at the proximal region of the catheter or at other portions of the catheter, e.g., at a distal end portion, where known imaging techniques would enable the user to discern when the indicator is turned on. It is also contemplated that in addition to providing an alert to the user in some embodiments, the pressure monitoring system can be tied into a system to directly reduce abdominal pressure so that if the pressure exceeds a threshold level (value), the abdominal pressure can automatically be reduced. In such systems, an indicator can be provided on the proximal portion of the catheter, e.g., at a proximal end outside the patient's body, or separate from the catheter. The sensor can be in communication with the indicator, either via connecting wires extending through a lumen of the catheter or a wireless connection. The sensor can be part of a system that includes a comparator so that a comparison of the measured pressure to a predetermined threshold pressure value is performed and a signal is sent to the indicator to activate (actuate) the indicator if the measured pressure exceeds the threshold pressure to alert the clinician or staff that pressure within the abdomen is too high and a signal is also sent to a device or system to automatically actuate the device or system to reduce the abdominal pressure. If the measured temperature is below the threshold, the indicator is not activated. A similar system can be used for temperature measurement and indication.

It is also contemplated that a micro-air charged sensor could be provided in the retention (stabilizing) balloon.

It is also contemplated that microtip sensors and/or fiber optic sensors can be utilized to measure pressure, and these sensors can be utilized instead of or in addition to the fluid pressure readings utilizing the aforedescribed balloon(s) for measuring pressure.

Pulse oximeters for measuring oxygen levels (oxygen saturation) in the urethral and/or bladder tissue could also be provided. In some embodiments, the pulse oximetry sensors can be positioned on the catheter proximal to the retention balloon. Alternatively, the sensors can be positioned within the retention balloon, on the catheter distal to the pressure balloon or on other regions of the catheter. Another channel in the catheter can be provided for the sensor and its connector to external devices, e.g. readers.

The catheters disclosed herein are designed for insertion into the bladder. However, it is also contemplated that they can be adapted for insertion into the rectum, colostomy pouch, stomach, supra-pubic bladder drain, or other orifice directly connected with the abdominal cavity. They can also be inserted into other areas connected with other cavities. Uses include by way of example, cardiac use, labor and delivery use, rectal placement for abdominal cavity, use for gastric pressure, esophageal motility, endocranial pressures ERCP, gall bladder, etc.

Although the apparatus and methods of the subject invention have been described with respect to preferred embodiments, those skilled in the art will readily appreciate that changes and modifications may be made thereto without departing from the spirit and scope of the present invention as defined by the appended claims.

What is claimed is:

1. A catheter configured to be inserted into a cavity of a patient for monitoring pressure, the catheter comprising:
   a first lumen having a wall and at least one side opening in the wall configured for drainage from the cavity;
   a second lumen;
   an expandable first balloon at a distal portion of the catheter, the second lumen communicating with the first balloon, the first balloon having a distal portion and a first outer wall, the first balloon receiving fluid to move from a first condition to a more expanded condition, in the first condition, the balloon having the distal portion protruding distally of the catheter to cover a tip of the catheter and a proximal portion within the catheter, and upon expansion of the first balloon, the first balloon exits a distal opening of the catheter and expands radially distally of the distal opening, the first balloon having a fluid containing chamber configured to monitor pressure within the cavity of the patient as pressure on the first outer wall of the first balloon deforms the first balloon and compresses the fluid within the first balloon; and
   a pressure sensor communicating with the fluid containing chamber for measuring pressure based on compression of the fluid caused by deformation of the first balloon resulting from deformation of the first balloon.

2. The catheter of claim 1, wherein the catheter comprises an exit port for passage of air from an interior of the first balloon to outside the catheter and a membrane having a plurality of pores dimensioned to enable passage of the air but prevent passage of the fluid.

3. The catheter of claim 1, wherein the catheter comprises an additional lumen and a stabilizing balloon, the additional lumen communicating with the stabilizing balloon to inflate the stabilizing balloon to stabilize a position of the catheter, the stabilizing balloon positioned proximal of the expandable first balloon.

4. The catheter of claim 3, wherein the first balloon and the stabilizing balloon are composed of different materials.

5. The catheter of claim 1, wherein the first balloon in the first condition forms a nose cone shape.

6. The catheter of claim 1, wherein the first balloon elongates out of the catheter as it opens up.

7. The catheter of claim 6, wherein the proximal portion of the first balloon has a smaller diameter such that the distal opening of the catheter is open for drainage.

8. The catheter of claim 1, further comprising a temperature sensor.

9. The catheter of claim 8, wherein the temperature sensor is within the first balloon.

10. The catheter of claim 1, wherein the first balloon has a coating to change a modulus of the first balloon.

11. The catheter of claim 6, wherein the first balloon has a coating to reduce permeability.

12. The catheter of claim 1, further comprising a pulse oximetry sensor to measure oxygen saturation.

13. The catheter of claim 3, wherein the side opening is distal of the stabilizing balloon.

14. The catheter of claim 13, wherein the proximal portion of the first balloon has a smaller diameter such that the distal opening of the catheter is open for drainage.

15. The catheter of claim 14, wherein the first balloon in the first condition forms a nose cone shape.

16. The catheter of claim 7, wherein the catheter comprises an exit port for passage of air from an interior of the first balloon to outside the catheter and a membrane having a plurality of pores dimensioned to enable passage of the air but prevent passage of the fluid.

17. The catheter of claim 3, where the first balloon has a different configuration than the stabilizing balloon.

* * * * *